United States Patent
Yoo

(10) Patent No.: US 6,711,750 B1
(45) Date of Patent: Mar. 30, 2004

(54) BELT FOR ACUPRESSURE

(76) Inventor: Dong-hoon Yoo, 807, 1-Dong, Hanyang Apt., 32-5, Banpo-Dong, Seocho-Ku, Seoul (KR)

( * ) Notice: Subject to any disclaimer, the term of this patent is extended or adjusted under 35 U.S.C. 154(b) by 0 days.

(21) Appl. No.: 10/307,708

(22) Filed: Dec. 2, 2002

(30) Foreign Application Priority Data

Sep. 23, 2002 (KR) .................................. 2002-0028464 U

(51) Int. Cl.$^7$ .............................. A41F 3/02; A61B 17/00
(52) U.S. Cl. ........................... 2/338; 601/134; 606/204
(58) Field of Search .............................. 2/338, 467, 69, 2/44, 311–322, 326, 336, 171, DIG. 11; 128/95.1, 96.1, 99.1–102.1, 875, 876; 602/19, 20, 23; 601/134, 132, 135, 143–144; 606/204, 189, 201, 204.15

(56) References Cited

U.S. PATENT DOCUMENTS

| | | | | |
|---|---|---|---|---|
| 1,605,959 A | * | 11/1926 | Lefevre | 601/143 |
| 3,605,731 A | * | 9/1971 | Tigger | 128/845 |
| 4,022,197 A | * | 5/1977 | Castiglia | 602/61 |
| 4,411,258 A | * | 10/1983 | Pujals, Jr. | 601/134 |
| 4,479,495 A | * | 10/1984 | Isaacson | 606/204 |
| 5,338,290 A | * | 8/1994 | Aboud | 602/75 |
| 5,445,647 A | * | 8/1995 | Choy | 606/204 |
| 5,470,304 A | * | 11/1995 | Decanto | 601/134 |
| 5,695,520 A | * | 12/1997 | Bruckner et al. | 606/204 |
| 5,848,981 A | * | 12/1998 | Herbranson | 601/134 |
| 5,938,684 A | * | 8/1999 | Lynch et al. | 606/204 |
| 6,554,787 B1 | * | 4/2003 | Griffin et al. | 602/74 |
| 6,645,128 B1 | * | 11/2003 | Hur | 482/124 |

FOREIGN PATENT DOCUMENTS

JP            9224966     *  9/1997

* cited by examiner

Primary Examiner—Tejash Patel
(74) Attorney, Agent, or Firm—Richard M. Goldberg

(57) ABSTRACT

An elastic textile belt for acupressure, includes securing elements at opposite ends of the belt for securing the belt around the waist of a user; an abdominal acupressure element having a plurality of metal protrusions on the inner surface of the belt and a pouch for holding heat generating elements on an outer surface of the belt; a movable lumbar acupressure element having a plurality of metal protrusions on the inner surface, a plurality of hooks on the outer surface and a pouch for holding heat generating elements between the surfaces.

5 Claims, 8 Drawing Sheets

BELT FOR ACUPRESSURE

BACKGROUND OF THE INVENTION

The present invention relates to a belt for acupressure, and more particularly, to a belt for acupressure comprising an elastic textile belt which comprises securing elements at opposite ends of the belt for securing the belt around the waist of a user, an abdominal acupressure element having a plurality of metal protrusions on an inner surface, pouches for holding heat generating elements on an outer surface and a plurality of metal protrusions formed at several places of the inner surface, and a movable lumbar acupressure element which comprises a plurality of metal protrusions on the inner surface, a plurality of hooks on the outer surface and a pouch for holding heat generating elements between these surfaces. The movable lumbar acupressure element can be inserted onto the textile belt via said hooks.

Generally, a belt is made from elastic fabrics and has securing elements at opposite ends. Such belt merely provides a pressure effect to lumbar and abdominal portions. Even though an elastic fabric belt having a magnet, a nonferrous metal, and a mineral inserted inside has been used, particular effects from properties of those materials are not sufficient. Furthermore, those materials have the property of getting cold when they contact the skin. Thus, the belt cannot be worn for a long period of time. In order to solve this drawback, a belt having a heating wire inserted inside to keep it warm has been used. However, this belt has the drawbacks that its structure is complicated and electronic waves harmful to the human body are emitted.

Korean Utility Model application No. 2002-17374, which was filed by the present applicant, and which is the subject of corresponding U.S. patent application Ser. No. 10/217,208, filed Aug. 12, 2002, relates to a belt which comprises a plurality of metal protrusions and a pouch formed on the lumbar and abdominal acupressure portions and provides acupressure and warming effects by inserting heat generating elements into said pouch. However, the belt of this prior application can only be used by a limited number of users because the plurality of metal protrusions formed on the lumbar and abdominal acupressure portions are fixed. When a user who has a waist either thinner or thicker than the given belt size wears it, only one of the lumbar and abdominal portions can receive acupressure by the plurality of metal protrusions and heat generating elements. Thus, the belt of the prior application has limited usage and is uneconomical because various sizes of the belts are required depending on the waist thickness.

There has thus been a need of users for a belt which can be used by anyone irrespective of man, woman, child and age.

SUMMARY OF THE INVENTION

The present invention was designed to solve the aforementioned problems.

An object of the present invention is to provide a belt which can adjust acupressure portions depending on a user's waist size and give an effective acupressure effect at a proper position as well as a warming effect.

In order to attain the above object, a belt of the present invention comprises an elastic textile belt which comprises securing elements at opposite ends of the belt for securing the belt around the waist of a user, an abdominal acupressure element having a plurality of metal protrusions on an inner surface, pouches for holding heat generating elements on an outer surface and a plurality of metal protrusions formed at several places of the inner surface, and a movable lumbar acupressure element which comprises a plurality of metal protrusions on the inner surface, a plurality of hooks on the outer surface and a pouch for holding heat generating elements between these surfaces.

Since the movable lumbar acupressure element can be inserted into the belt via said hooks, the belt of the present invention can be worn in a state in which a plurality of metal protrusions are positioned on the lumbar portion and an abdominal acupressure element is positioned on the abdominal portion, regardless of the waist thickness of the user. Accordingly, the belt of the present invention can provide an acupressure effect by the metal protrusions on the lumbar and abdominal portions, as well as a warming effect by heat from heat generating elements.

BRIEF DESCRIPTION OF THE DRAWINGS

The above and other objects and features of the present invention will be hereinafter explained in detail with reference to the accompanying drawings.

DESCRIPTION OF THE PREFERRED EMBODIMENTS

Figure 6:
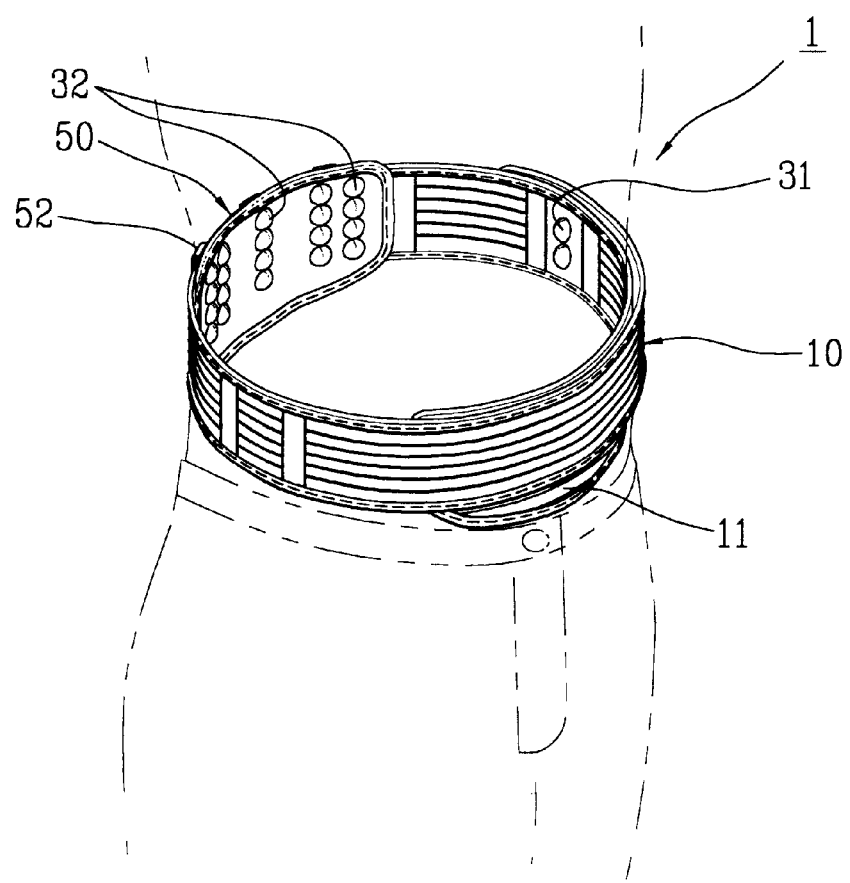
FIG. 6 is an illustrated view showing a-state of wearing the present invention.

The present invention relates to a belt for acupressure which includes an elastic textile belt 10 comprising securing elements 20, 21 at opposite ends of the belt for securing the belt around the waist of a user, an abdominal acupressure element 11 having a plurality of metal protrusions 30 on the inner surface, a pouch 12 for holding heat generating elements 40 on the outer surface, a plurality of metal protrusions 31 formed at several places, and a movable lumbar acupressure element 50 which comprises a plurality of metal protrusions 32 on the inner surface, a plurality of hooks 52 on the outer surface and a pouch 51 for holding heat generating elements 40 between these surfaces. Since the movable lumbar acupressure element 50 can be inserted onto the belt 10 via said hooks 52, the belt 1 of the present invention can be worn in a state in which the movable lumbar acupressure element 50 is positioned on the lumbar portion and abdominal acupressure element 11 is positioned on the abdominal portion. When these elements are correctly positioned, the belt can be worn by using securing elements 20, 21 at opposite ends, as illustrated in FIG. 6. When belt 1 for acupressure is worn, the lumbar portion provides an acupressure effect by a plurality of metal protrusions 32 formed on the movable lumbar acupressure element 50 and a warming effect by heat from heat generating elements 40 inserted in pouch 51 of said element 50. Since said heat generating elements 40 contain iron powder and sodium chloride, they generate heat when reacting with oxygen in the air. An abdominal portion also provides acupressure and warming effects by metal protrusions 30 and heat generating element 40 on abdominal acupressure element 11. Also, a plurality of metal protrusions 31 formed at several places on the belt 10 exert acupressure on the skin.

Figure 7:
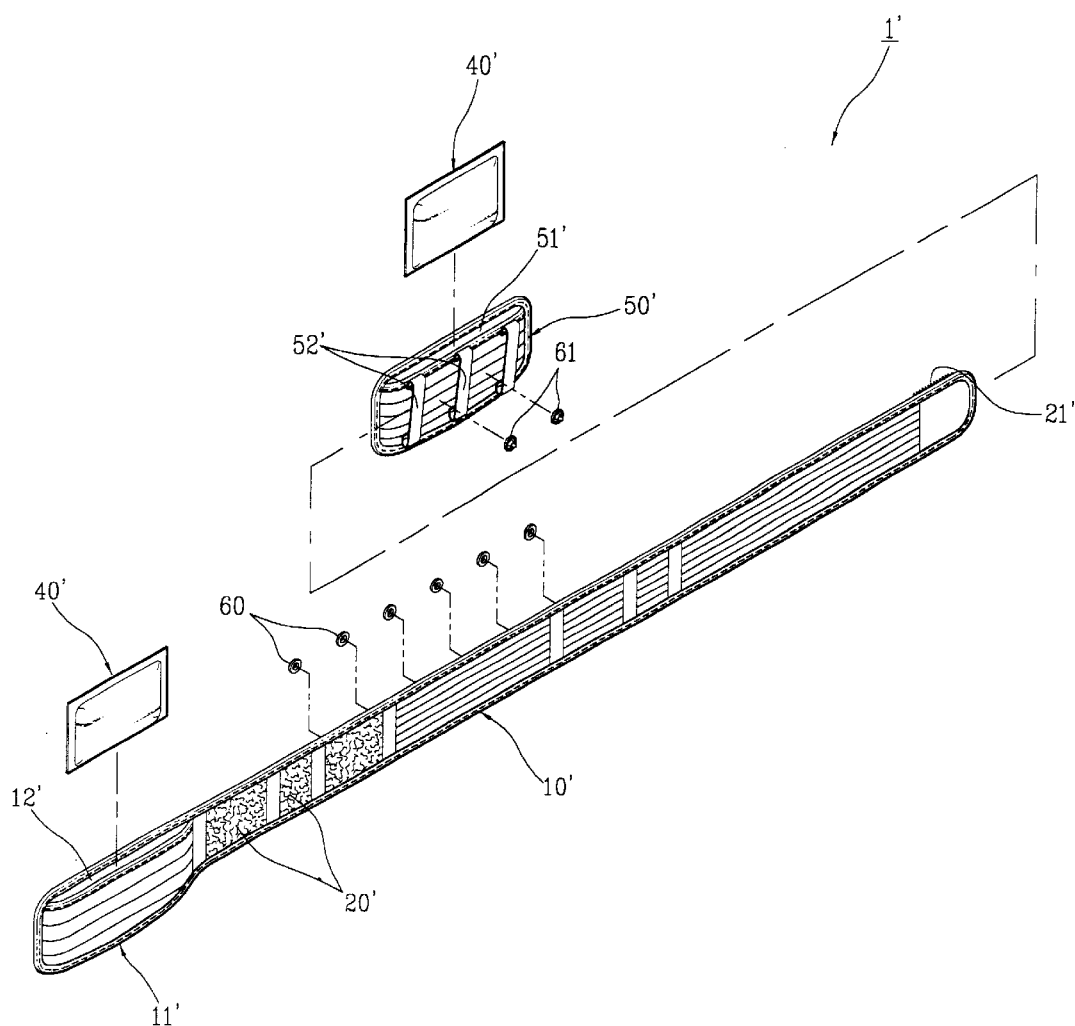
FIG. 7 is an exploded perspective view of a second embodiment of the present invention.
Figure 8:
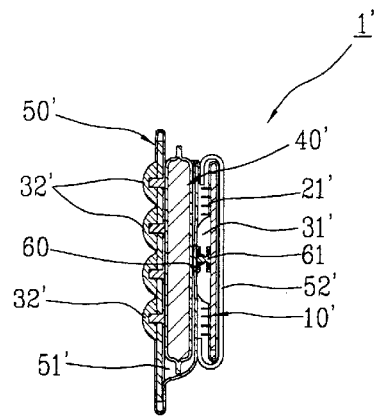
FIG. 8 is an enlarged cross-sectional view showing an important part of the second embodiment of the present invention.
Figure 9:
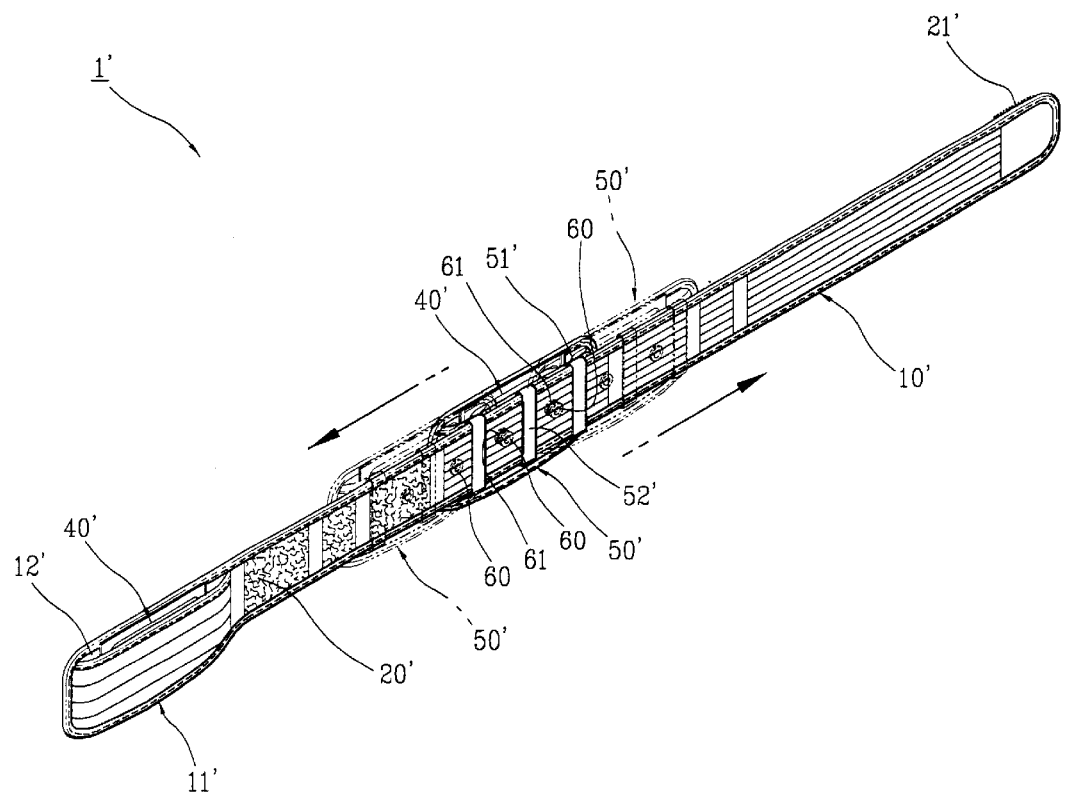
FIG. 9 is an illustrated view showing a state where a movable lumbar acupressure element of the second embodiment of the present invention is moving.

FIGS. 7–9 illustrate another embodiment of the present invention. The belt 1' according to the embodiment comprises an elastic textile belt 10' having a plurality of female buttons 60 at the lumbar portion and a movable acupressure element 50', which will be inserted onto the belt 10', having a plurality of hooks 52' and two male buttons 61 to be coupled with said female buttons 60. This belt 1' is worn by inserting the movable acupressure element 50' onto the belt 10' to be positioned on the lumbar portion, coupling female buttons 60 on the belt 10' with male buttons 61 on the movable acupressure element 50' and positioning the abdominal acupressure element 11' on the abdominal portion. By using the buttons 60, 61, said belt 1' can be simply worn with no movement of the movable acupressure element 50' after insertion onto the belt 10'.

Figure 10:
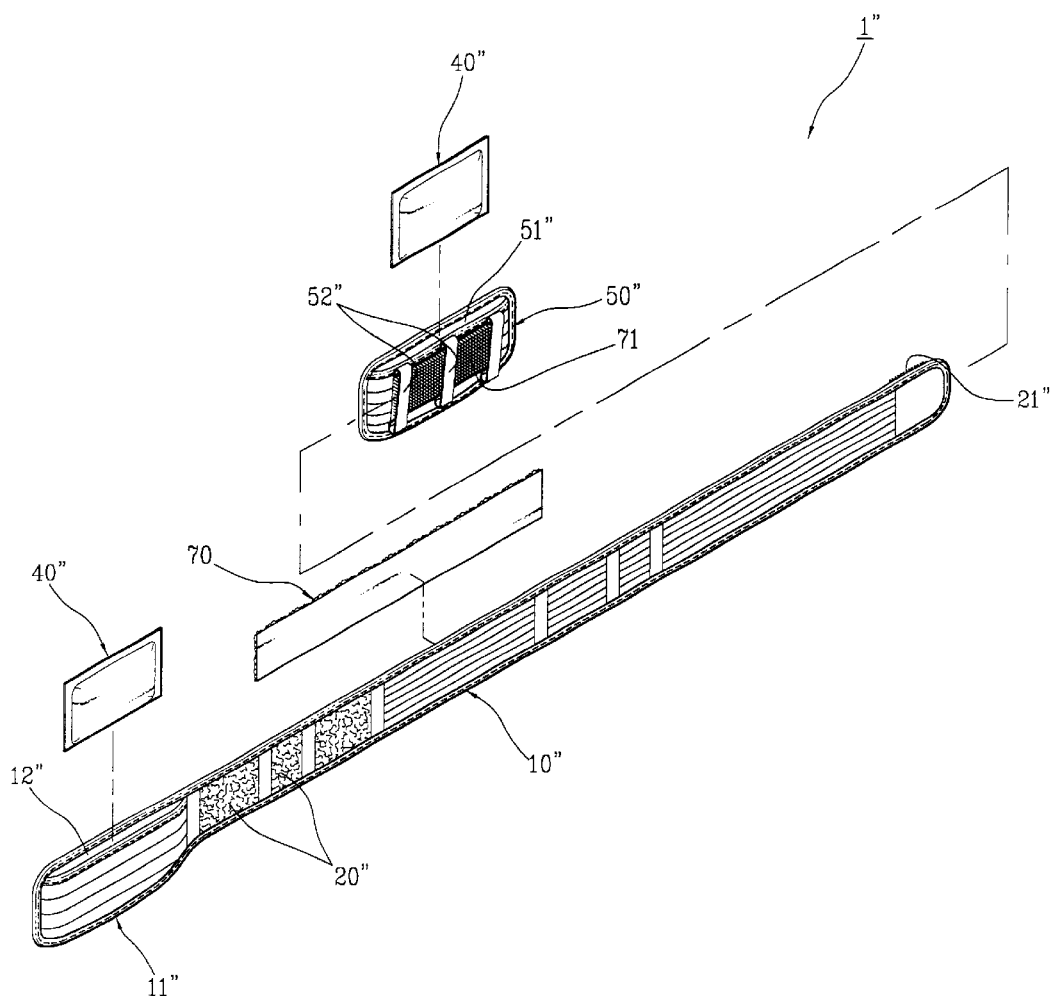
FIG. 10 is an exploded perspective view of a third embodiment of the present invention.
Figure 11:
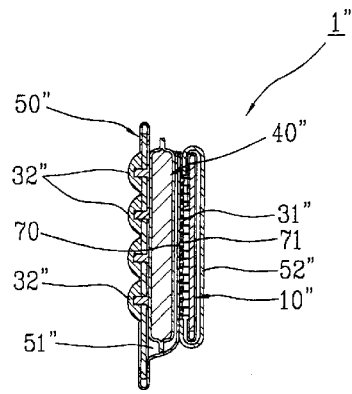
FIG. 11 is an enlarged cross-sectional view showing an important part of the third embodiment of the present invention.
Figure 12:
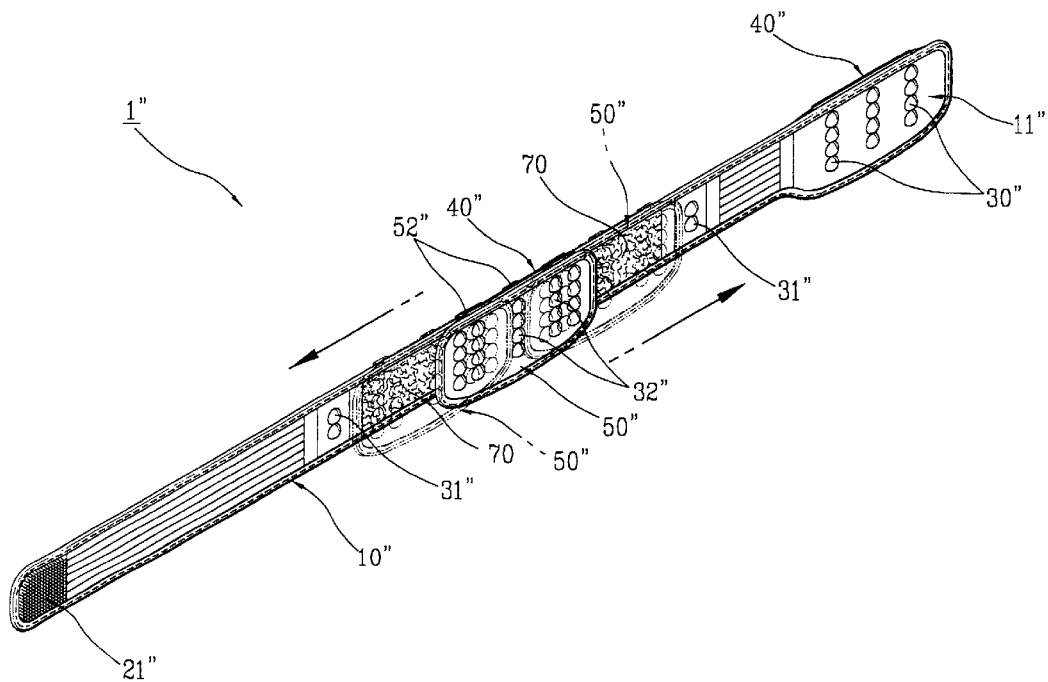
FIG. 12 is an illustrated view showing a state where a movable lumbar acupressure element of the third embodiment of the present invention is moving.

FIGS. 10–12 illustrate another embodiment of the present invention. The belt 1" according to the embodiment comprises an elastic textile belt 10" having a long hook patch 70 sold under the trademark "VELCRO" at the lumbar portion and a movable acupressure element 50", which will be inserted onto the belt 10", having a plurality of hooks 52" and a loop patch 71 sold under the trademark "VELCRO" to be coupled with said hook patch 70. This belt 1" is worn by inserting the movable acupressure element 50" onto the belt 10" to be positioned on the lumbar portion, coupling hook patch 70 on the belt 10" with loop patch 71 on the movable acupressure element 50" and positioning the abdominal acupressure element 11" on the abdominal portion. By using patches 70, 71, said belt 1" can be very simply worn with no movement of the movable acupressure element 50" after insertion onto the belt 10".

Figure 1:
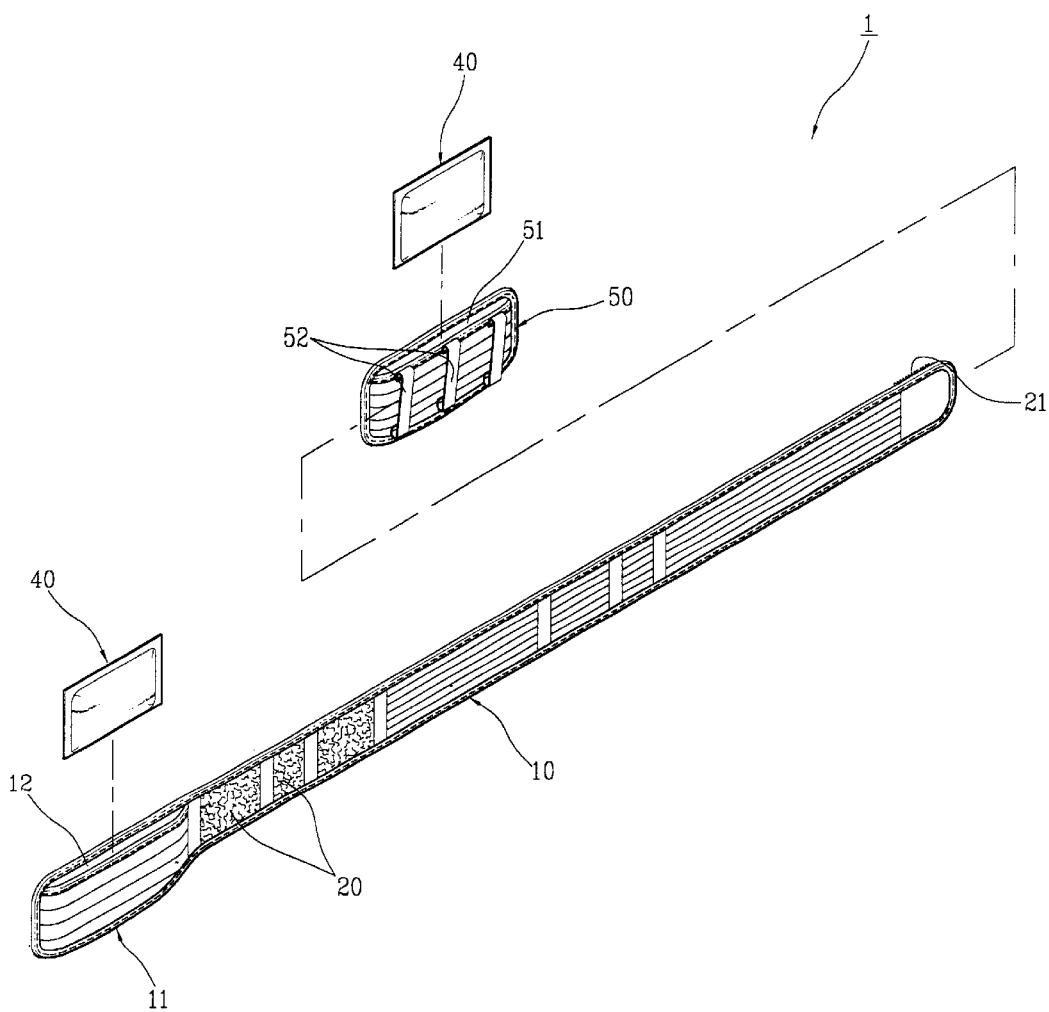
FIG. 1 is an exploded perspective view of the present invention.
Figure 2:
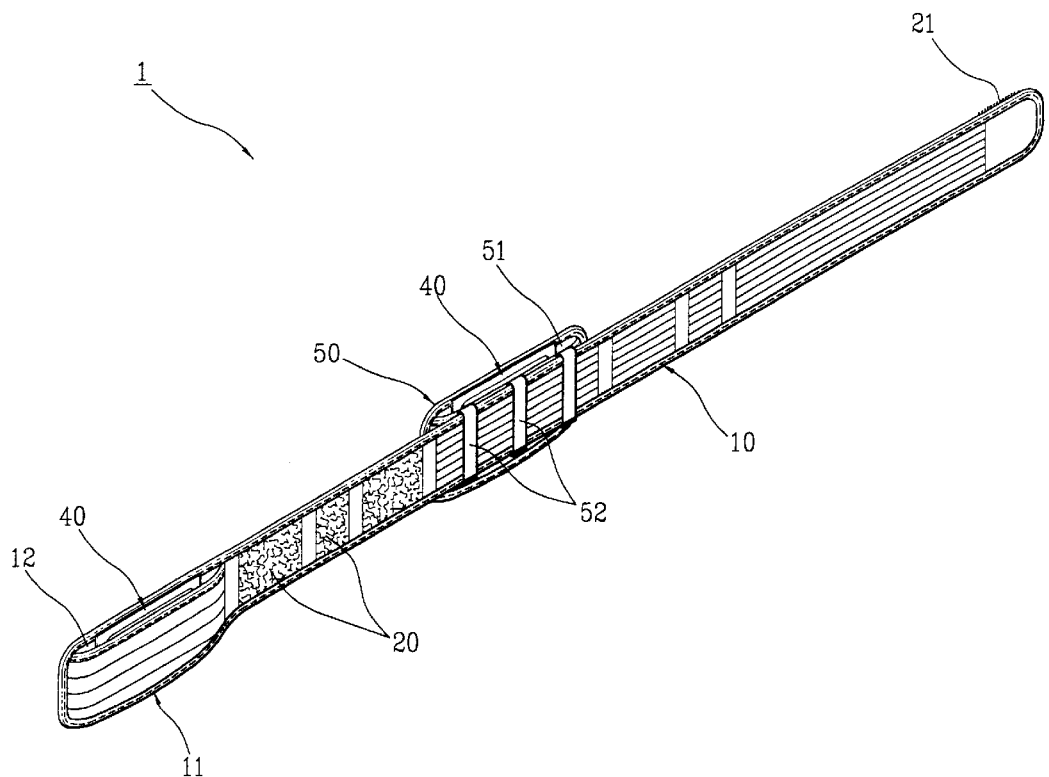
FIG. 2 is a combined perspective view of the present invention.
Figure 3:
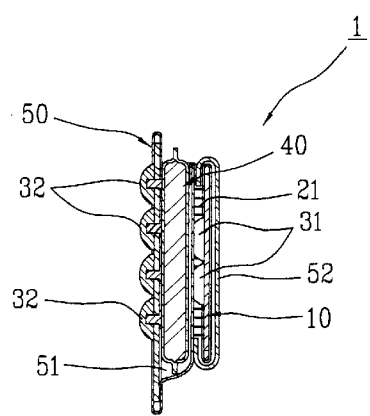
FIG. 3 is an enlarged cross-sectional view showing an important part of the present invention.
Figure 4:
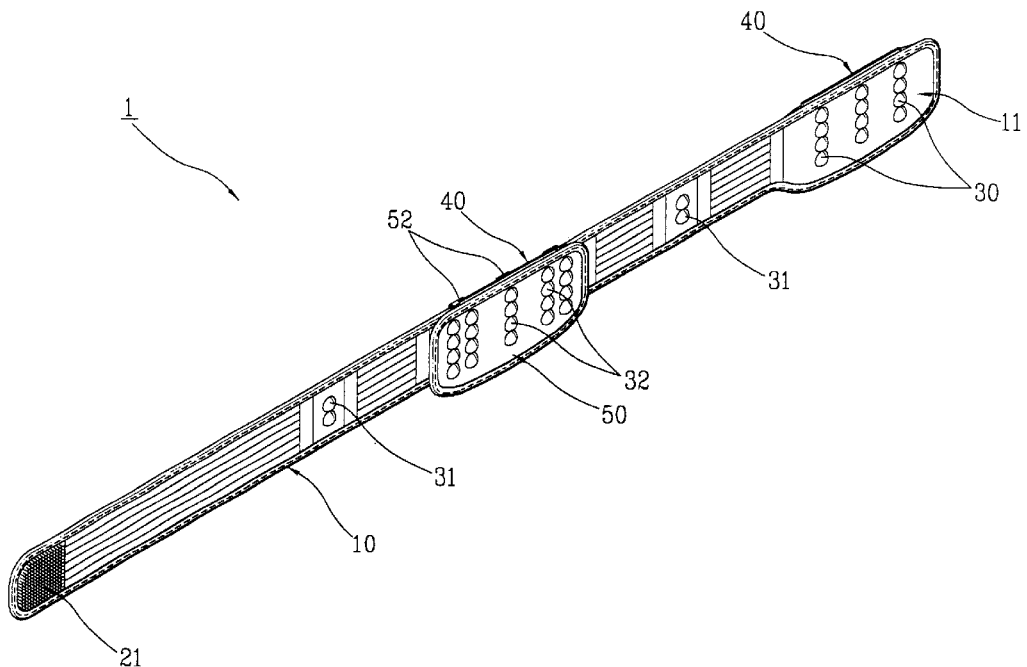
FIG. 4 is a rear perspective view of the present invention.
Figure 5:
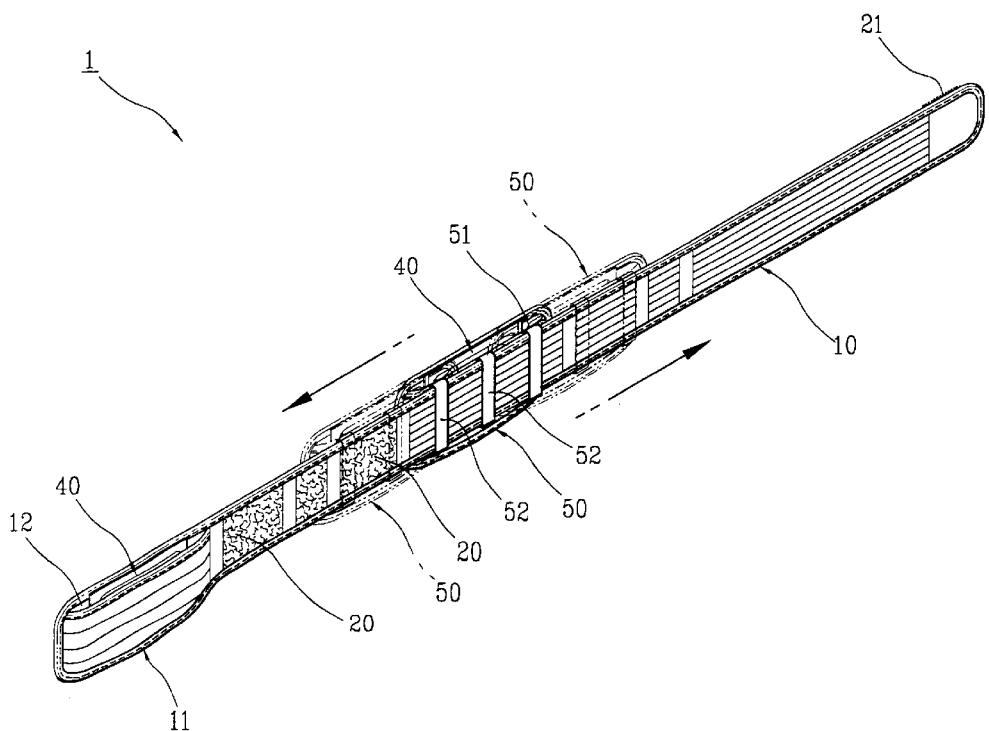
FIG. 5 is an illustrated view showing a state where a movable lumbar acupressure element of the present invention is moving.

As mentioned above, the belt 1 of the present invention comprises a movable acupressure element 50 inserted onto belt 10 and the movable acupressure element 50 can be moved right and left as illustrated in FIG. 5. Thus, belt 1 can be worn regardless of the waist thickness of the user by adjusting the movable acupressure element 50 to a lumbar position, as shown in FIG. 6. Accordingly, the belt 1 of the present invention has advantages that it can be easily worn and conveniently adjust the acupressure element to the lumbar position. Also, it provides an acupressure effect by a plurality of metal protrusions 32,30 formed on movable acupressure element 50 to be contacted with the lumbar portion and on abdominal acupressure element 11. It further provides a warming effect on lumbar and abdominal portions by heat generating elements 40 inserted into each pouch 51, 12 formed on the movable acupressure element 50 and abdominal acupressure element 11. The metal protrusions 31 formed at several places on the belt 10 also provide an acupressure effect on the skin.

As shown in FIG. 7, since movable acupressure element 50' can be combined with elastic textile belt 10' via buttons 60, 61, the belt 1' can be easily worn with no movement of the movable acupressure element 50'. As illustrated in FIG. 10, the belt 1" can be very easily worn with no movement of the movable acupressure element 50" via patches 70, 71. Thus, the belts according to the present invention are convenient to wear and practical.

What is claimed is:

1. A belt for acupressure comprising;
    an elastic textile belt including:
        an inner surface,
        an outer surface,
        securing elements at opposite ends of the belt for securing the belt around a waist of a user,
        an abdominal acupressure element having a plurality of metal protrusions on the inner surface,
        a pouch for holding a heat generating element on the outer surface, and
        a plurality of metal protrusions formed at several positions on the inner surface, and
    a movable lumbar acupressure element including:
        an inner surface,
        an outer surface,
        a plurality of metal protrusions on the inner surface of the movable lumbar acupressure element,
        an arrangement for securing said movable lumbar acupressure element on said textile belt for movement along the outer surface of the textile belt, and
        a pouch for a holding heat generating element between the inner and outer surfaces of the movable lumbar acupressure element.

2. A belt for acupressure according to claim 1, wherein said arrangement includes hooks which receive the elastic textile belt therethrough.

3. A belt for acupressure according to claim 2, further comprising mating button elements on the elastic textile belt and the movable lumbar acupressure element for releasably fixing the movable lumbar acupressure element to the elastic textile belt.

4. A belt for acupressure according to claim 1, wherein said arrangement includes one of a hook patch and a loop patch on the movable lumbar acupressure element and the other of a hook patch and a loop patch on the elastic textile belt, for releasably fixing the movable lumbar acupressure element to the elastic textile belt.

5. A belt for acupressure according to claim 1, wherein the at least one pouch is formed at the abdominal acupressure element.

\* \* \* \* \*

UNITED STATES PATENT AND TRADEMARK OFFICE
CERTIFICATE OF CORRECTION

| | | |
|---|---|---|
| PATENT NO. | : 6,711,750 B1 | Page 1 of 1 |
| APPLICATION NO. | : 10/307708 | |
| DATED | : March 30, 2004 | |
| INVENTOR(S) | : Tae Woo Yoo | |

It is certified that error appears in the above-identified patent and that said Letters Patent is hereby corrected as shown below:

On the face of the patent, please change the name of the Inventor in Item [76] to read "Tae Woo Yoo."

Signed and Sealed this

Twenty-ninth Day of August, 2006

JON W. DUDAS
*Director of the United States Patent and Trademark Office*